United States Patent [19]

Simon et al.

[11] Patent Number: 5,752,525
[45] Date of Patent: *May 19, 1998

[54] URETHRAL PLUG ASSEMBLY HAVING ADHESIVE FOR ENHANCED SEALING CAPABILITIES AND METHOD OF USING SAID PLUG ASSEMBLY

[75] Inventors: John G. Simon, Boston; Paul D. McLaughlin, Scituate, both of Mass.; Leo C. Felice, Pascoage, R.I.; Sharad Joshi, Watertown; Azhar Syad, Boston, both of Mass.

[73] Assignee: UroMed Corporation, Needham, Mass.

[*] Notice: The term of this patent shall not extend beyond the expiration date of Pat. No. 5,509,427.

[21] Appl. No.: 566,732

[22] Filed: Dec. 4, 1995

Related U.S. Application Data

[63] Continuation of Ser. No. 124,264, Sep. 20, 1993, which is a continuation-in-part of Ser. No. 62,592, May 15, 1993, Pat. No. 5,483,976, and Ser. No. 88,469, Jul. 7, 1993, which is a continuation-in-part of Ser. No. 811,571, Dec. 20, 1991, Pat. No. 5,479,945, said Ser. No. 62,592, is a continuation-in-part of Ser. No. 811,571, which is a continuation-in-part of Ser. No. 746,364, Aug. 16, 1991, which is a continuation-in-part of Ser. No. 636,285, Dec. 31, 1990, Pat. No. 5,090,424.

[51] Int. Cl.$^6$ ........................................... A61F 5/48
[52] U.S. Cl. ..................... 128/885; 128/DIG. 25; 600/29
[58] Field of Search ................ 128/885, DIG. 26; 604/329, 330, 346–353; 600/29–31

[56] References Cited

U.S. PATENT DOCUMENTS

| | | | |
|---|---|---|---|
| 2,324,520 | 7/1943 | Lamson | 128/283 |
| 2,494,393 | 1/1950 | Lamson | 128/1 |
| 2,638,093 | 5/1953 | Kulick | 128/133 |
| 3,503,400 | 3/1970 | Osthagen et al. | 128/349 |
| 3,646,929 | 3/1972 | Bonnar | 128/1 |
| 3,726,277 | 4/1973 | Hirschman | 128/285 |
| 3,789,828 | 2/1974 | Schulte | 128/1 R |
| 3,797,478 | 3/1974 | Walsh et al. | 128/1 R |
| 3,841,304 | 10/1974 | Jones | 128/1 R |

(List continued on next page.)

FOREIGN PATENT DOCUMENTS

| | | |
|---|---|---|
| WO 8810106 | 12/1988 | WIPO. |
| WO 8900030 | 1/1989 | WIPO. |
| WO 9004431 | 5/1990 | WIPO. |
| WO 9219192 | 11/1992 | WIPO. |

OTHER PUBLICATIONS

Nielsen et al., "The Urethral Plug: A New Treatment Modality For Genuine Urinary Stress Incontinence in Women", copyright 1990, pp. 1199–1202, Journal of Urology, vol. 144.

*Primary Examiner*—Michael A. Brown
*Attorney, Agent, or Firm*—Lorusso & Loud

[57] ABSTRACT

A novel urethral plug assembly having adhesive thereon, wherein the adhesive seals the plug assembly against an internal wall thereby arresting movement of the plug assembly while it functions in the urethra to block the flow of urine therefrom. The plug assembly may comprise a solid body which is of a sufficient diameter to occlude the urethra. Alternatively, the plug assembly may comprise a body which has the ability to change its shape from a compressed to an elongated condition so as to conform to the urethral wall and occlude the opening to the urethra. In one embodiment of the invention, the adhesive lies on the meatal plate of the plug assembly so as to secure the plug assembly against the meatus urinarius. In a second embodiment of the invention, the adhesive is on the body of the plug assembly so as to seal the plug assembly against the urethra, bladder neck or bladder wall. In a third embodiment of the invention, the adhesive is on a portion of the meatal plate so as to seal the plug assembly at the tissue surrounding the meatus urinarius. The adhesive seals the plug assembly in place until the wearer wishes to void, at which point, the seal may be broken by the exertion a downward, pulling force on the plug assembly.

23 Claims, 6 Drawing Sheets

U.S. PATENT DOCUMENTS

| | | | |
|---|---|---|---|
| 3,857,394 | 12/1974 | Alemany | 128/260 |
| 4,019,499 | 4/1977 | Fitzgerald | 128/1 R |
| 4,258,704 | 3/1981 | Hill | 128/1 |
| 4,261,340 | 4/1981 | Baumel et al. | 128/1 |
| 4,428,365 | 1/1984 | Hakky | 128/1 |
| 4,457,299 | 7/1984 | Cornwell | 128/1 R |
| 4,553,533 | 11/1985 | Leighton | 128/1 |
| 4,563,183 | 1/1986 | Barrodale | 604/349 |
| 4,682,592 | 7/1987 | Thoregard | 128/303 R |
| 4,822,347 | 4/1989 | MacDougall | 604/329 |
| 4,846,784 | 7/1989 | Haber | 600/29 |
| 4,850,963 | 7/1989 | Sparks et al. | 600/29 |
| 4,938,759 | 7/1990 | Enscore et al. | 604/896.1 |
| 4,946,449 | 8/1990 | Davis, Jr. | 604/256 |
| 4,981,465 | 1/1991 | Ballan et al. | 600/32 |
| 5,012,822 | 5/1991 | Schwarz | 128/885 |
| 5,074,855 | 12/1991 | Rosenbluth et al. | 604/385.1 |
| 5,090,424 | 2/1992 | Simon et al. | 128/885 |
| 5,097,848 | 3/1992 | Schwarz | 128/885 |
| 5,114,380 | 5/1992 | Larsen | 452/176 |
| 5,114,398 | 5/1992 | Trick et al. | 600/29 |
| 5,116,387 | 5/1992 | Berg | 623/66 |
| 5,131,906 | 7/1992 | Chen | 600/29 |
| 5,234,409 | 8/1993 | Goldberg et al. | 604/96 |
| 5,336,208 | 8/1994 | Rosenbluth et al. | 604/329 |
| 5,483,976 | 1/1996 | McLaughlin et al. | 128/885 |
| 5,509,427 | 4/1996 | Simon | 128/885 |

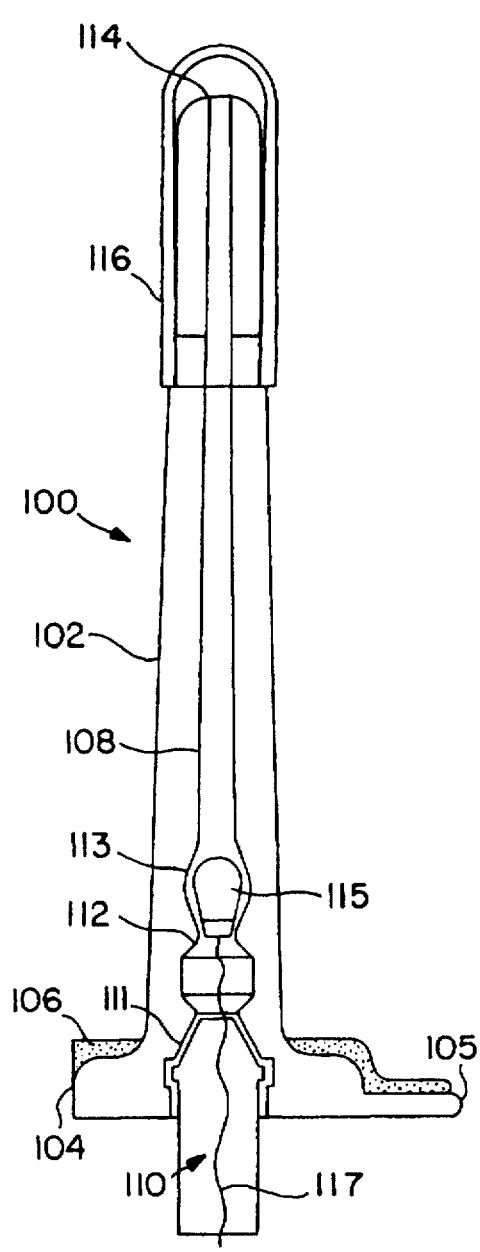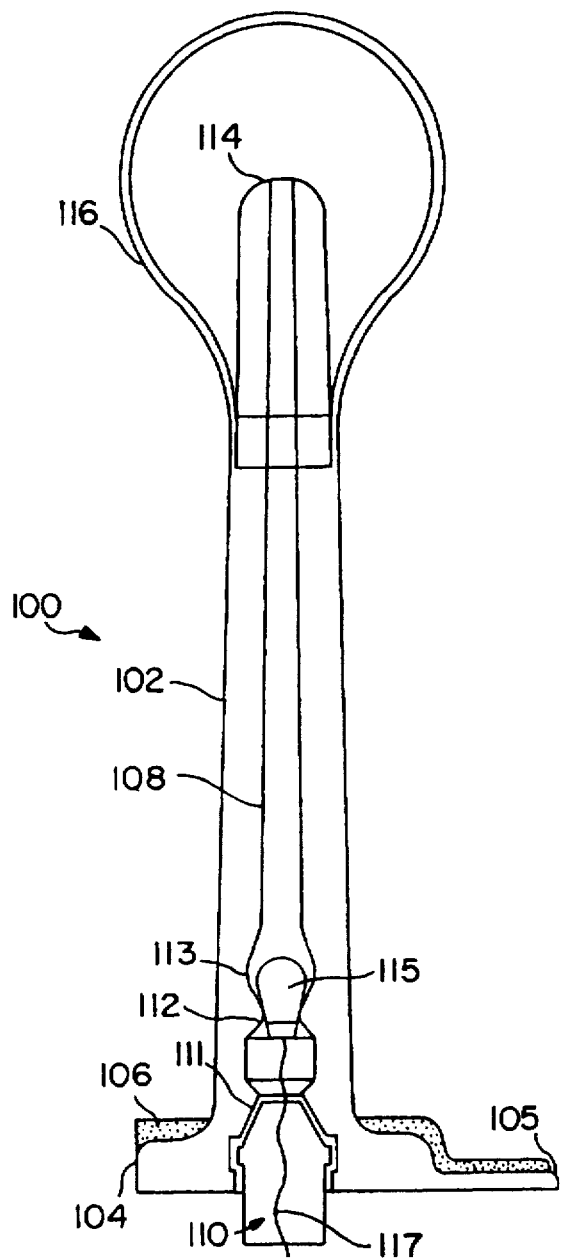
FIG. 2A
FIG. 2B

URETHRAL PLUG ASSEMBLY HAVING ADHESIVE FOR ENHANCED SEALING CAPABILITIES AND METHOD OF USING SAID PLUG ASSEMBLY

CROSS REFERENCE TO A RELATED APPLICATION

The present application is a continuation of application Ser. No. 08/124,264, filed Sep. 20, 1993, which is a continuation-in-part of application U.S. Ser. No. 08/062, 592, filed May 15, 1993, U.S. Pat. No. 5,483,976, and application U.S. Ser. No. 08/088,469 filed Jul. 7, 1993, both of which are a continuation-in-part of application U.S. Ser. No. 811,571, filed Dec. 20, 1991, U.S. Pat. No. 5,479,945, which is a continuation-in-part of application U.S. Ser. No. 746,364, filed Aug. 16, 1991, which is a continuation-in-part application of U.S. Ser. No. 636,285, filed Dec. 31, 1990, now U.S. Pat. No. 5,090,424.

BACKGROUND OF THE INVENTION

1. Technical Field of the Invention

This invention relates to a urethral plug assembly having an adhesive coating thereon, enabling it to maintain stability in the urethra.

2. Description of the Prior Art

Urinary stress incontinence is defined as the involuntary loss of urine when the pressure within the urethra exceeds the maximum urethral pressure required for maintaining closure. While the problem of urinary incontinence occurs in men and women, it is an affliction especially common in women of child bearing age and beyond.

There are in existence many methods used to address the problem of incontinence. Bladder neck suspension surgery, wherein the neck of the bladder is reduced by suspending the bladder, is perhaps the most desirable way to treat incontinence, especially in younger patients. However, there are numerous risks associated with such surgery, notwithstanding the expense. For some patients, surgery is not recommended for medical or other reasons, and for those with mild incontinence surgery is not an appropriate solution.

As an alternative to surgical correction, devices have been developed to address the problem of urinary incontinence. Many of these devices require surgery for implantation, and of these surgically implanted devices, there are two distinct types: non-manipulable devices and manipulable devices. One such non-manipulable device, described in U.S. Pat. No. 4,019,499, is a capsule filled with a variable amount of fluid. The capsule is surgically implanted between supporting tissue and the urethra to exert an occluding force thereon. A similar, non-manipulable capsule implant is described in U.S. Pat. No. 3,789,828. However, this device has ties extending therefrom to aid in fiber ingrowth, thus providing mechanical stability to the capsule. One problem associated with this device is the risk of fluid leakage. In addition to problems with leakage, severe tissue damage may result from the unnatural method in which such devices regulate incontinence.

Other surgically implanted devices exist which are manipulable. These devices provide the wearer with the ability to selectively control the operation of the device via manually operable elements implanted in the tissue surrounding the urethra. U.S. Pat. No. 4,428,365, and U.S. Pat. No. 4,846,784 each disclose an indwelling device having an inflatable chamber with an attached tubing and an inflation bulb. The wearer may manually adjust the pressure exhibited by the inflatable member on the urethra, simply by squeezing the tissue encasing the bulb. These devices, however, often produce thickening and scarring of surrounding tissue, making their usefulness questionable. Additional adverse effects associated with surgically implanted indwelling devices, whether non-manipulable or manipulable in nature, are encrustation, irritation and infection.

There are also known in the art certain indwelling devices that do not require surgical implantation. These devices are inserted by a physician through the urethral orifice and allow the wearer to void either past or through the device. An example of such a device is disclosed in U.S. Pat. No. 4,850,963 in which a physician inserts a bolus of ferromagnetic material through the urethra and into the bladder. The bolus rests at the juncture of the bladder and urethra and is moved for bladder evacuation, by the relative positioning of a magnet across the body of the wearer. However, the bolus may become lodged in an area beyond the reaches of the magnetic force exhibited by the magnet, making the device inoperative. Another example of this type of indwelling device is the prestressed capsule disclosed in U.S. Pat. No. 4,457,299. The capsule is inserted by a physician within the lower interior of the urethra and is set at a prestressed pressure slightly above involuntary pressure. When the urine pressure exceeds the preset pressure of the capsule, the capsule deforms allowing urine to flow around the device. This device, however, has no feature to prevent migration of the device into the bladder. In U.S. Pat. No. 4,553,533 there is shown a prosthetic urethral sphincter valve which is placed in the urethra and anchored in the bladder. The patient increases his bladder pressure by means of a valsalva maneuver, and holds this pressure while the valve activates. Urine may then pass through the valve with the valve later returning to its closed position. This device is very complicated, expensive, difficult to manufacture and uncomfortable. Another physician-inserted device is disclosed in U.S. Pat. No. 3,797,478. This device has an expandable collar which is inflated after insertion, by an injection of fluid therein. When it is desired to remove the device, the inflated collar is ruptured or serrated, thus expelling the fluid into the wearer's body. Notwithstanding the cumbrous use of this device, there is a risk of infection associated with the release of injection fluid upon removal. Similarly, U.S. Pat. No. 3,841,304 discloses a plug which is inserted by a physician into the urethra and subsequently inflated to block the flow of urine. This device may be left in the body for extended periods. After insertion, the device merely requires repositioning in the urethra to permit bladder evacuation. Such a device leaves the wearer susceptible to infection, as bacteria may be introduced into the urethra during repositioning, or during indwelling time. Also, serious complications can occur upon removal, when a separate wire must be inserted therein. These devices being indwelling, are often cumbersome to the wearer and often cause numerous complications such as encrustation, irritation and infection.

Also known in the art are devices capable of being inserted by the wearer into the urethra. Such devices are removed for voiding, and then reintroduced into the urethra upon completion of bladder evacuation. An example of such a device is the solid-type urethral plug, described by Neilsen, Kurt K. et al., in "The Urethral Plug: A New Treatment Modality for Genuine Urinary Stress Incontinence in Women" J. Urology, vol. 44, p. 1100 (1990). This device consists of one or two solid spheres located along a soft shaft, and a thin, soft plate located at the end of the shaft.

One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra so that the sphincter can operate. When the patient wants to evacuate the bladder, the plug is removed, evacuation occurs, and a fresh plug is inserted. One problem associated with this device is that the patient must have three urethral closure pressure profiles performed as well as other examinations, before the device is made for the wearer. Additional problems associated with this device include placement difficulties, lack of sealing capabilities associated therewith, inadequate retention thereby allowing expelling and inadequate anchoring by the plate at the meatus. In addition, such problems is the discomfort associated with insertion and removal, due to the size profile and rigidity of the spheres, which maintain a constant diameter during insertion, and removal. Another "remove-to-void" device is disclosed in U.S. Pat. No. 5,090,424, which comprises a conformable urethral plug. The body of the plug forms a cavity which is in fluid communication with another cavity via a check-valve. Thus, fluid may be pumped into the cavity within the urethra to provide a custom fit. This device, like many others relying on liquids or gels for expansion, relies heavily on a fluid-tight valve in order to maintain retention. Should valve failure occur, evacuation would immediately follow. There is also a chance of fluid leakage into the body of the wearer should rupture of the plug occur.

There are also known in the art certain external devices that do not require insertion into the urethra. Urine absorbing pads have been developed to collect and absorb urine as it flows out of the body. Such pads have difficulty retaining a stationary position and often lack effectiveness in preventing leakage. An example of an external device in which such problems have been addressed is the urine absorbing pad disclosed in U.S. Pat. No. 5,074,855. This device employs adhesive to secure a pad to the vestibule such that urine is absorbed as it is expelled from the body. However, there are many disadvantages associated with such a device. Urine buildup in the urethra creating an uncomfortable sensation for the wearer is one such disadvantage. Additionally, due to the structure and function of such a device, there is nothing to increase urethral resistance to urine flow. Moreover, as such a pad is designed only to be worn externally, it is subject to migration in the course of one's daily movement and activities, even with the use of adhesive given the friction associated with undergarments contacting the pad. Migration as such, increases the likelihood of accidents and leakage. Although this pad attempts to seal and absorb urine at the meatus, the meatus is not physiologically blocked thus the wearer is susceptible to discomfort and leakage. This device, given its structure and composition, would not be effective internally due to the differing physiological conditions present in the urethra, bladder neck or bladder, where internal conditions such as high temperature and moisture levels exist.

As evidenced by the above discussion, problems associated with the stability of urinary incontinence devices have not been adequately addressed in the prior art. Prior art devices have focused solely on sizing a device such that the urethra is occluded, without addressing the need for enhancing the retention and sealing capabilities of such devices.

In view of the above problems associated with the prior art, an easily manipulable, "remove-to-void", indwelling urethral plug assembly having enhanced retention and sealing capabilities would be desirable to those afflicted with urinary incontinence.

SUMMARY OF THE INVENTION

One object of the invention is to improve the degree of retention of a urethral plug assembly in the urethra.

A further object of the invention is to enhance the sealing ability of a urethral plug assembly with the urethral, bladder neck, or bladder wall.

Another object of the invention is to enhance the sealing ability of a urethral plug assembly at the urethral meatus, such that migration into the bladder will not occur.

Another object of the invention is to prevent slippage of the urethral plug assembly while disposed in the urethra.

Another object of the invention is to continuously block the flow of urine in the event of malfunction of the plug assembly.

Another object of the invention is to reduce the risk of contamination to the wearer of a urethral plug assembly.

Yet another object of the invention is to provide a device which is easily used by the wearer.

Another object of the invention is to increase the urethral resistance to urine flow through the urethra.

Still another object of the invention is to provide a method for controlling urinary incontinence.

These and other objects of the invention are carried out by a novel urethral plug assembly having adhesive thereon, wherein the adhesive seals the plug against the meatus urinarius, or alternatively, the urethral, bladder neck or bladder wall. The plug may comprise a solid body which is of a sufficient diameter to allow occlusion of the urethra to prevent incontinence. Alternatively, the plug may comprise a body which has the ability to change its shape. One such plug assembly may comprise a member comprising a body having a lumen for accepting fluid from an external syringe, and delivering such to a fluidly inflatable balloon. The fluid may be a liquid or gel, or air. Such a plug is to be inserted while the balloon is in a non-inflated position. After insertion, fluid can be introduced into the lumen via a syringe, from where it travels through a valve to inflate and distend the balloon thereby occluding the urethra, bladder neck or bladder. Another type of plug assembly may comprise a mechanically expandable housing and cooperating inner member, lying in coaxial engagement and possessing a contracted diameter for insertion and removal through the orifice of the urethra, and a larger, expanded diameter for blocking the flow of urine in the urethra, bladder neck and bladder. A larger diameter is achieved by mechanical deployment of the inner member resulting in a change in the shape of the housing. This change in shape causes the external surface to expand, which seals the plug assembly to the urethral, bladder neck or bladder wall. Alternatively, the plug may comprise a condition-responsive expandable member having the ability to possess an expanded condition when exposed to a physiological condition such as body temperature, moisture, or pH. The adaptation of the condition responsive plug to the expanded condition occurs automatically without actuation of the plug by the wearer.

In each of the above plug assemblies, the portion of the plug that functions to block the flow of urine is the body, and the portion of the plug that serves to anchor the plug at the meatus urinarius, is the meatal plate. Removal of the plug assembly for bladder evacuation, is easily accomplished by either pulling a cord causing the contraction of the plug assembly and/or grasping a tab associated with said meatal plate. The meatal plate serves to prevent migration of the plug assembly into the bladder.

In one embodiment of the invention, an adhesive layer lies meatal plate so as to secure the plug against the meatus urinarius. In a second embodiment of the invention, an adhesive layer lies on the body of the plug so as to seal the plug against the urethra, bladder neck or bladder wall. In a third embodiment of the invention, an adhesive layer lies on the outer circumference of the meatal plate so as to seal the plug against the tissue surrounding the meatus urinarius. These and other advantages will be better appreciated from the detailed description that follows.

BRIEF DESCRIPTION OF THE DRAWINGS

FIG. 2A shows a fluidly expandable urethral plug assembly having adhesive on its meatal plate, in a deflated state.

FIG. 2B shows a fluidly expandable urethral plug assembly having adhesive on its meatal plate, in an inflated state.

DETAILED DESCRIPTION OF THE PREFERRED EMBODIMENTS

Figure 1:
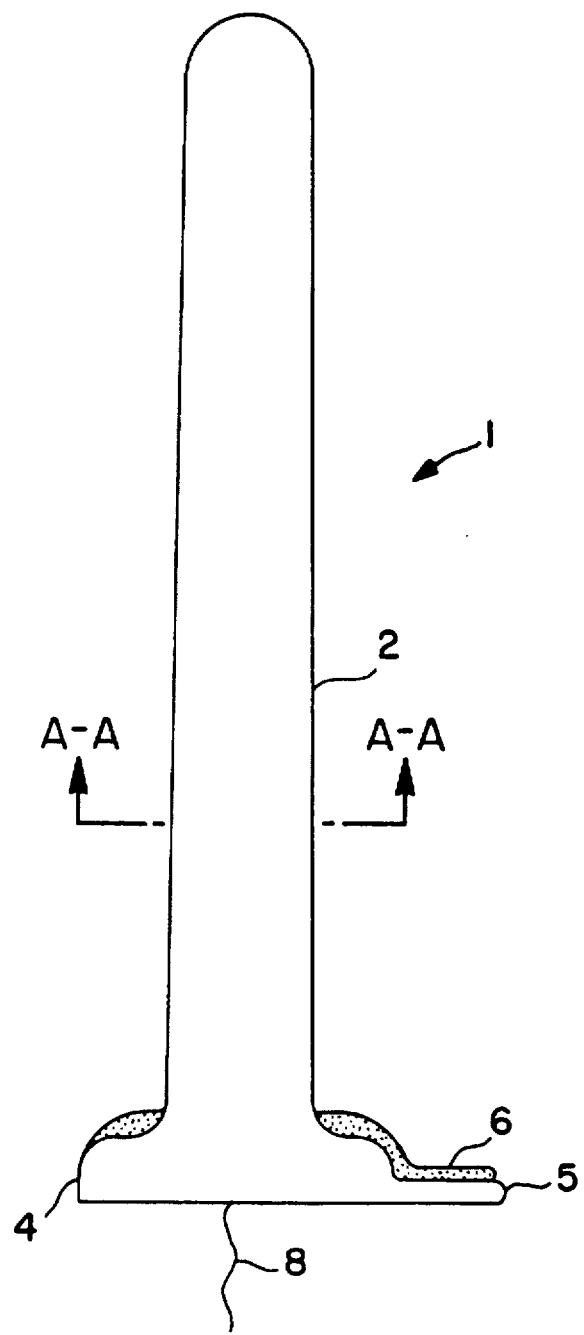
FIG. 1 shows a solid urethral plug having adhesive on the meatal plate.

Referring first to FIG. 1, shown is a solid plug assembly 1, having a body 2 sized to allow occlusion of the urethra following insertion. A meatal plate 4 is disposed at the distal end of the body which prevents migration of the plug assembly 1 into the bladder. The meatal plate 4 is a flanged type member, having a tab 5 which prevents migration of the plug assembly 1 into the bladder and aids in removal of the plug assembly 1 when the wearer wishes to void. The meatal plate 4 anchors the plug assembly at the meatus urinarius. To carry out this function of anchoring, the meatal plate 4 is of a thickness sufficient to withstand bodily compression during wear, preferably on the order of one millimeter or greater. On the meatal plate 4, is a layer of adhesive 6, preferably a hydrogel adhesive. This layer 6 seals the meatal plate 4 at the meatus urinarius after insertion of the plug into the urethra, thereby ensuring a firm and secure placement of the plug assembly 1. A string 8 extends from the body for removal of the plug assembly 1 after insertion. Alternatively, removal may be carried out by the tab 5, a ring (not shown), or another removal member may be adapted to extend from the body 2. Line A—A represents the cross sectional view of the body 2, which will be discussed further with reference to FIGS. 7A and 7B.

The operation of the plug assembly 1 is such that upon insertion, the urethral wall conforms thereto, via an automatic reflex motion. The meatal plate 4, anchoring the plug assembly 1 at the meatus urinarius further provides a seal therewith, via the adhesive layer 6. This seal prevents slippage of the assembly 1 from its position in the urethra, thereby ensuring continuous blockage of urine. Note that the adhesive layer 6, although shown to be continuous, may be discontinuous depending on the degree of adhesion desired.

FIG. 2A shows a fluidly expandable urethral plug assembly 100 in a deflated state. The plug assembly 100 has a body 102 with a meatal plate 104 on its distal end, and an expandable balloon 116 at its proximal end. The body 102 wall is relatively constant in outer diameter allowing the device to be easily inserted. The meatal plate 104, as in the embodiment of FIG. 1 has a layer of adhesive 106 thereon. The internal portion of the body 102 of the plug assembly defines a lumen 108, a first cavity 111, and a valve seat 113. The fluid responsible for inflating balloon 116 is introduced from an external syringe 110 adapted to be inserted in the first cavity 111. The fluid can be any fluid capable of being pumped from the syringe 110 with sufficient force to displace a ball 115 resting against valve seat 113. The meatal plate 104 and tab 105, like the meatal plate 104 as previously discussed in the above embodiment, is adapted to anchor the urethral plug assembly 100 at the meatus urinarius. The layer of adhesive 106 lies on the meatal plate 104 so as to form a seal with the meatus after insertion.

FIG. 2B shows the urethral plug assembly 100 after the fluid has been pumped into the balloon 116, such that the plug assembly 100 is in an inflated state. Inflation is carried out by inserting syringe 110 into the plug assembly 100 so that it lies within the first cavity 111. Fluid is then expelled from the syringe 110 for travel through the first cavity 111 to the valve seat 113, whereby the force of the fluid pushes the ball 115 off the valve seat 113 thereby providing a continuous flow path from the first cavity 111 to the lumen 108. The fluid thus travels freely from syringe 110 through the valve seat opening 112 and into lumen 108. The fluid then continues to travel out of the opening 114 of lumen 108, whereupon it inflates the balloon 116. When the balloon 116 is inflated, the expulsion of fluid from syringe 110 may be terminated and the syringe 110 removed. At this point, the ball 115 falls back against valve seat 113 to occlude valve seat opening 112, thus closing such opening 112 off from external fluid entry or exit. Thus the fluid contained in the balloon 116 functions to maintain the plug assembly in its inflated state for urine blockage. When it is desired to remove the plug assembly, the wearer deflates the balloon 116 by simply pulling on the cord 117 attached to the ball 115, causing the ball 115 to dislodge and pass from the valve seat opening 112 toward the distal end of the plug assembly 100. Although such action results in the expulsion of fluid from the balloon 116, the seal between the plug assembly 100 and the meatus remains intact due to the adhesive 106 on the plate 104, which continues to block the flow of urine. The wearer may then comfortably remove the plug assembly 100 as the diameter thereof is reduced. Removal is accomplished by a continuous tug on the tab 105, which serves to break the seal and disengage the meatal plate 104 from the meatus.

Figure 3B:
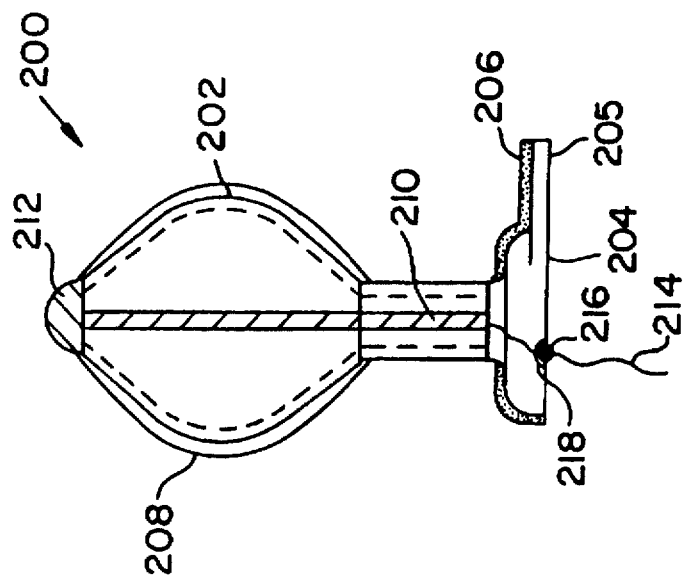
FIG. 3B shows a mechanically expandable urethral plug assembly having adhesive on its meatal plate, in an expanded state.
Figure 3A:
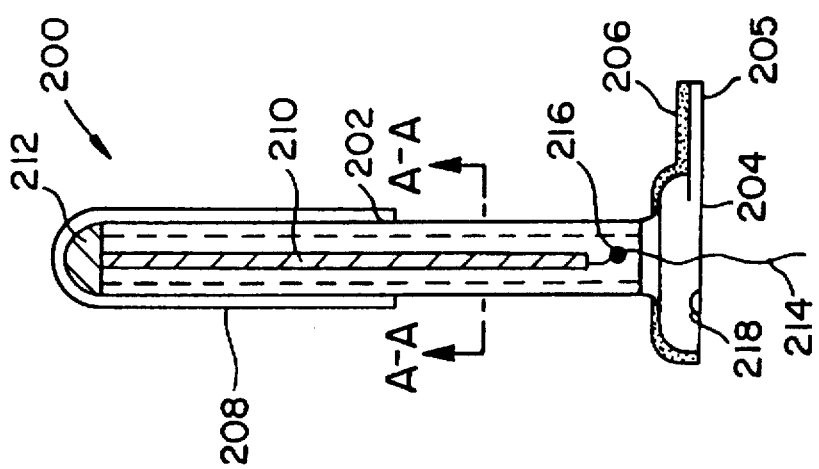
FIG. 3A shows a mechanically expandable urethral plug assembly having adhesive on its meatal plate, in a contracted state.

FIG. 3A like FIG. 2A, shows an expandable plug assembly 200 also having a layer of adhesive 206 on its meatal plate 204. Plug assembly 200, has a body 202 comprised of a hollow, cylindrical tube which is sized to be easily inserted through the orifice of the urethra. The tube 202 is made from a biocompatible material having characteristics of compressibility. Attached on the periphery thereof either by thermal bonding, laminating or other means, is a balloon 208 which is adapted to rest against the tube 202. At the distal end of the tube is a meatal plate 204 having a tab 205. The meatal plate 204, like the meatal plates previously discussed, is adapted to anchor the urethral plug assembly 200 at the meatus urinarius. A layer of adhesive 206 lies on the meatal plate 204 so as to form a seal with the meatus after insertion. Referring again to FIG. 1, enclosed within the tube is a support rod 210, which may be a hollow or a solid member. The support rod 210 has a bulb 212 at one end thereof, abutting the proximal end of the tube. The bulb 212 functions to hold the support rod within the tube. The support rod 212 has a cord 214 attached at its end opposite the bulb 212, which extends through the tube 202 and beyond the meatal plate 204, thus ensuring that a wearer will always be able to reach the cord 214. On the cord 214 there is preferably formed a knot 216. Although the knot 216 has been used, the attachment of any member having a diameter greater than ball retention socket 218 in meatal plate 206 would suffice. The support rod 210 is formed of a biocompatible material, the tube 202 is preferably formed of a biocompatible thermoplastic material and the balloon 208 is preferably a biocompatible thermoplastic elastomer, such as that sold under the trademark KRATON. However, any biocompatible material may be used for each of the aforementioned elements, as the invention is not to be limited to those named above. Line A—A represents the cross sectional view of the tube, which will be discussed further with reference to FIGS. 7A and 7B.

The operation of the plug assembly 200 is described in connection with FIG. 3B. A user inserts the plug assembly 200 while it is in a contracted configuration. Once the plug assembly 200 has been inserted, the meatal plate 204 abuts the meatus urinarius and the adhesive layer 206 forms a seal with the meatus. At this point, the plug assembly 200 may be deployed by the wearer, whereupon it achieves an expanded configuration. To deploy, the wearer pulls on the cord 214 depending from the support rod 210. By pulling on cord 214, a downward force is exerted on the cord 214 in the vertical direction, forcing the support rod 210 to slide downwardly in the tube 202 and exert a compressive force against the proximal end of the outer tube 202. The tube 202 thus expands outwardly in the horizontal direction, causing the balloon 208 to expand until the balloon 208 forms a seal with the wall of the urethra, bladder neck or bladder. The wearer then secures the cord 216 by sliding it through a slit in the ball retention socket 218 located on the meatal plate 204. This causes the knot 216 to act as a stop, as the knot 216 rests within the socket 218, thereby preventing the tube 202 from returning to its contracted state. The expansion of the tube 202 serves to block the flow of urine as the balloon 208 forms a seal with the urethral, bladder neck or bladder wall. The placement of the plug assembly 200 is further retained in this position by the seal formed by the adhesive layer 206 on the meatal plate 204 with the meatus.

The plug assembly 200 in an expanded form, functions to block the flow of urine from the body. When the wearer wishes to remove the plug assembly 200, a simple tug on the cord 214 in a direction away from the socket 218 will cause the knot 216 to be released therefrom, thus causing the tube 202 to retract. The tube 202 thereby returns to its original diameter prior to insertion, making plug removal a comfortable task. Thus, the tube 202 and balloon 208 cooperatively provide an expandable housing and the plug includes means for mechanically expanding the housing and selectively returning the housing to its non-expanded condition. The seal between the adhesive layer 206 on the meatal plate 204 and the meatus, is then broken by the continuous downward pulling of the cord 214. At this point, the plug assembly may be removed and bladder evacuation may occur.

Figure 4B:
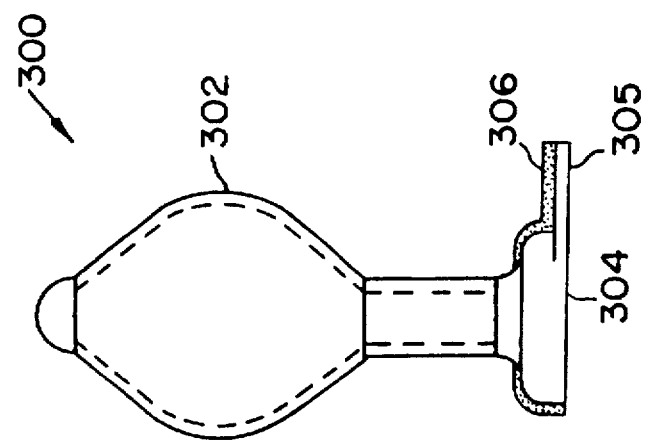
FIG. 4B shows a condition-responsive, expandable urethral plug assembly having adhesive on its meatal plate in an expanded state.
Figure 4A:
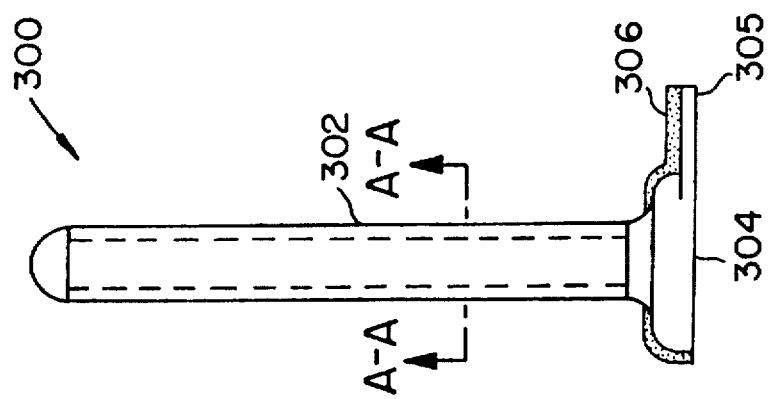
FIG. 4A shows a condition-responsive, expandable urethral plug assembly having adhesive on its meatal plate in an elongated state.

Referring now to FIG. 4A, a plug assembly 300 is shown, which is preferably formed of a biocompatible thermoplastic material. In a preferred embodiment, the plug 300 is made of a tube 302 of known polyurethane-based polymer which provides the plug 300 with shape memory. The unique characteristic of the plastic polymer is its automatically triggered shape memory, which allows the tube constructed of the shape memory polymer to be inserted into the urethra in a relatively compressed and elongated state, and regain a useful shape in response to a selected transition temperature, that being body temperature. The shape memory material however, may alternatively comprise a hydrophillic material (not shown) capable of expanding in response to moisture or pH gradations. Like the above embodiments, the tube 302 terminates in a meatal plate 304 which has a layer of adhesive 306 thereon. For purposes of illustration only, the ability of plug assembly 300 to expand due to changes in temperature, will be discussed.

When the urethral plug shown in FIG. 4A is subjected to a transition temperature, the relatively rigid plug 300 changes to a second condition in which it is flexible and easily deformable. The plug 300 is now pliable and, remembering its "mold shape plug", able to expand significantly in diameter to conform to the shape of the wearer's urethra. The expansion results in the formation of a tight seal between the urethra, bladder neck or bladder wall and the plug 300. The adhesive layer 306 also forms a seal between the plug 300 and the meatus. Thus the plug 300 is retained in the urethra to block the flow of urine.

In accordance with the above discussion, the operation of the plug is discussed in reference to FIG. 4B. The user inserts the urethral plug 300 of the present invention into the urethra while it is in its compressed and elongated state. The plug 300 is inserted until the meatal plate 304 abuts the meatus urinarius. At this point the layer of adhesive 306 on the meatal plate 304 forms a seal with the meatus urinarius. The plug 300, now lying in the urethra, is exposed to the heightened temperature of the human body. The temperature increase causes the shape memory polymer comprising the tube 302 to automatically expand outwardly and achieve a protrusion to conform to the size and shape of the wearer's urethra. The shape memory polymer is able to freely adapt and conform to its environment, the urethra, as it is only capable of expanding and conforming to the environment into which it is placed; it is incapable of exerting a resistive force by itself. This important characteristic of the shape memory polymer prevents displacement of the urethra, bladder neck or bladder by the shape memory polymer material.

As urine accumulates in the bladder, pressure from the accumulating urine builds until the bladder is sufficiently full to exert a downward force on the urine in the bladder neck and urethra. The downward force in turn bears down on the proximal portion of the expanded member of the plug 300, furthering the diametrical expansion of the proximal portion of the member. The expansion of the plug, in its expanded form, provides a tight seal with the wall of the urethra, bladder neck or bladder to retain the plug in the wearer's body. When the wearer wishes to remove the plug to void, a continuous tug on tab 305 of the meatal plate 304 will cause the rubbery, diametrically expanded member to elongate, and will break the seal formed between the adhesive layer 306 on the meatal plate 304 and the meatus. The tube 302 is then returned to a smaller diameter and is simply withdrawn from the body. Other means for removal of the plug is contemplated, such as but not limited to, a pulling means, such as a cord or ring (not shown), whereby the plug is simply removed by pulling on a cord attached to the plug. The ease with which the shape memory polymer plug allows removal prevents discomfort potentially associated with plug removal.

Figure 5:
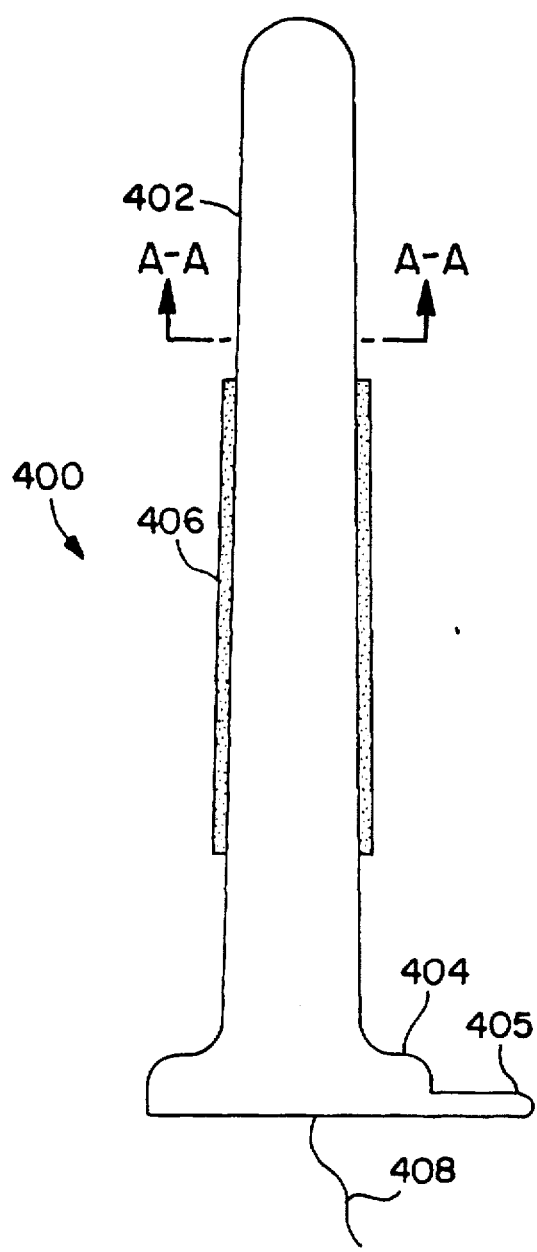
FIG. 5 shows a urethral plug assembly having adhesive on a portion of its body.

FIG. 5 shows an alternative embodiment of the invention with a urethral plug assembly 400 having an adhesive layer 406 on a portion of its body 402. For purposes of example only, the solid plug of FIG. 1 will be employed to illustrate this embodiment. Note, however, that the use of an adhesive layer as shown in this figure is to be applied to all of the aforementioned plug assemblies. In contrast with the plug assembly of FIG. 1, this plug assembly may or may not have an adhesive layer on the meatal plate 404. Instead, an adhesive layer 406 is found on a portion of the body 402 of the plug assembly 400, or, alternatively, with reference to FIGS. 3A and 3B, may be found on a balloon attached to the body. The adhesive layer located in such position, secures the placement of the plug assembly 400 in the urethra. Upon insertion of the plug assembly 400 into the urethra, the adhesive layer 406 bonds with the urethral, bladder neck or bladder wall, such that the walls conform to the plug assembly 400. This results in a tight sealing effect, such that the plug assembly 400 is prevented from moving in any direction. Moreover, with respect to the embodiments of FIGS. 2B and 3B, should the expansion of balloon 116 or tube 202, respectively, no longer function in the expanded state while placed in the urethra, due to valve or mechanical failure, the seal provided between a portion of the plug assembly and the urethra, bladder or bladder neck remains intact. If the wearer wishes to void, removal is carried out in much the same manner as in the above embodiments. The tab 405 of the meatal plate 404, and/or the string 408 associated with the plug is grasped and pulled downward, which serves to break the seal formed between the portion of the body and the urethral, bladder neck or bladder wall. Note that although this figure shows a continuous layer of adhesive 406, such a layer may be discontinuous, spotty or uneven, depending upon the degree of adhesion desired.

Figure 6:
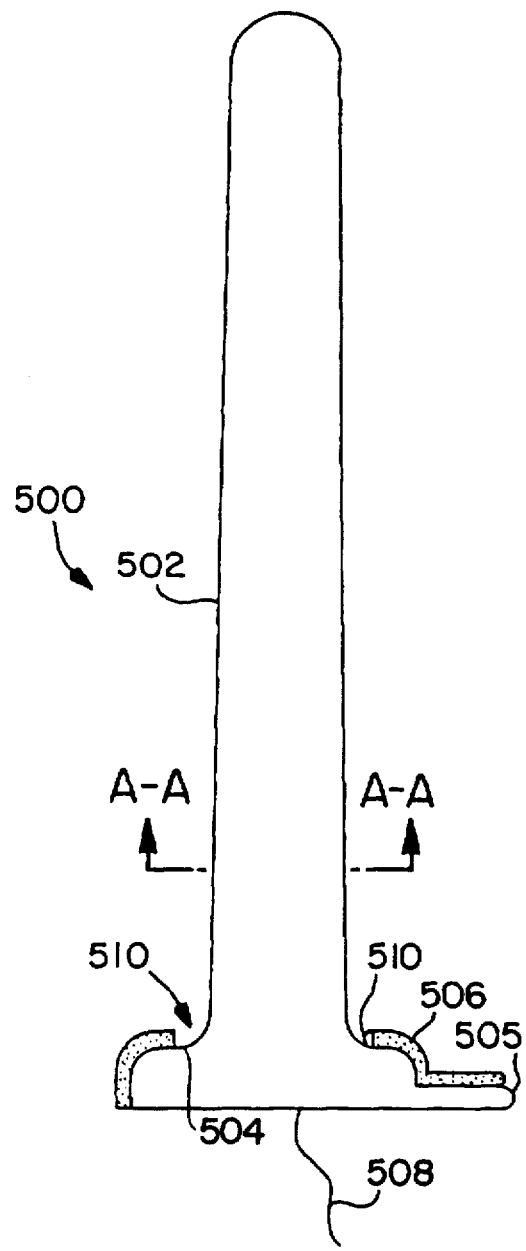
FIG. 6 shows a urethral plug assembly having adhesive on a portion of the meatal plate.

FIG. 6 shows an alternative embodiment of the invention, and for purposes of illustration only, the solid plug of FIG. 1 is shown for this embodiment of the invention. In this embodiment a urethral plug assembly 500 has a meatal plate 504 with a layer of adhesive 506 thereon. The adhesive layer 506 is positioned on the meatal plate 504 so as to seal the plug assembly 500 with the tissue surrounding the meatus. As shown, the adhesive layer 506 lies on a the outer circumferential portion of the meatal plate 504, such that a space 510 exists between the adhesive layer 506 and the body 502 of the plug assembly 500, the space 510 being free of adhesive. The plug assembly 500 with the adhesive layer 506 so positioned, functions to seal the plug at a distance from the meatus urinarius. When the wearer wishes to void, removal is carried out in much the same manner as in the above embodiments. The tab 505 of the meatal plate 504, and/or the string 508 is grasped and pulled downward, which serves to break the seal formed between a portion of the meatal plate 504 and the tissue surrounding the meatus urinarius. As with the aforementioned embodiments, note that although this figure shows a continuous layer of adhesive 506, such a layer may be discontinuous, spotty or uneven, depending upon the degree of adhesion desired. Moreover, this embodiment may optionally include a layer of adhesive on the body 502 of the plug assembly 500.

Figure 7A:
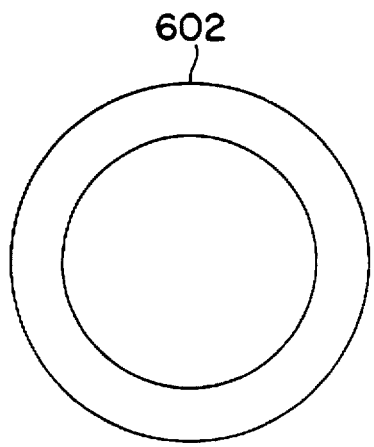
FIG. 7A shows an cross section along line A—A of the body of each of the urethral plug assemblies.
Figure 7B:
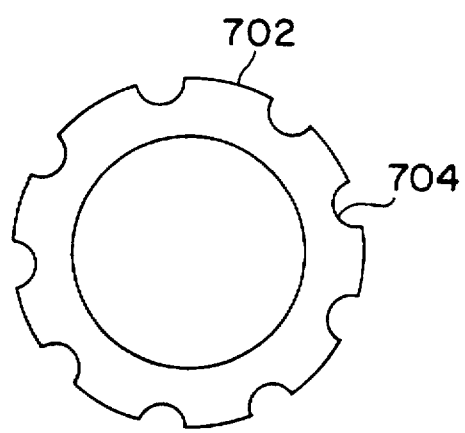
FIG. 7B shows an alter native cross section along line A—A of the body of each of the urethral plug assemblies.

FIG. 7A shows a cross sectional view of the urethral plug assembly along line A—A of the preferred embodiments set forth above. Body 602 is representative of elements 2, 102, 202, 302, 402 and 502 of the aforementioned plug assemblies, and as shown, is of a constant diameter. FIG. 7B shows an alternative embodiment of the urethral plug assembly, along line A—A. As shown, the diameter of body 702 is not constant but variant as shown by the curved indentations 704 on the periphery. The indentations 704 provide enhanced surface area by which the plug assembly may more readily adapt to the urethral, bladder neck or bladder wall. Such enhanced sealing ability of the plug assembly, provides a better fit for the wearer.

Figure 8:
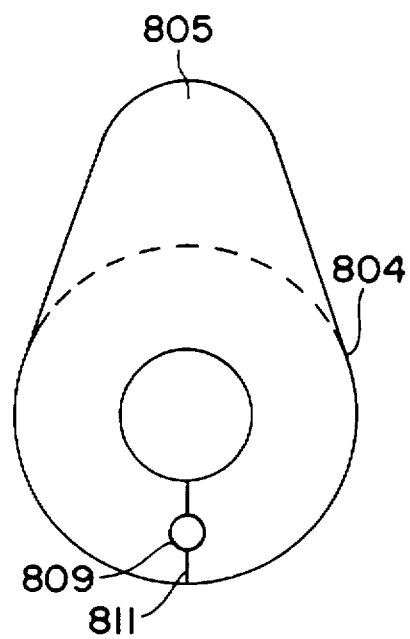
FIG. 8 shows a perspective view of the meatal plate of each of the urethral plug assemblies.

FIG. 8 shows a bottom perspective view of the meatal plate 804, which is the same as meatal plates 4, 104, 204, 304, 404, and 504, respectively discussed in the aforementioned embodiments. A portion of the meatal plate 804 is extended so as to form a tab 805 which may be grasped by the wearer for ease of removal. The meatal plate 804 may additionally have a ball retention socket 809 and slit 811 formed therein, particularly with respect to FIG. 3B so as to aid in maintaining the plug's expanded configuration.

While the invention has been particularly shown and described with reference to the aforementioned embodiments, it will be understood by those skilled in the art that various changes in form, composition and detail may be made therein without departing from the spirit and scope of the invention. Thus, any modification to the shape, configuration and/or composition of the elements comprising the invention is within the scope of the present invention.

What is claimed is:

1. A remove-to-void device for controlling urinary incontinence comprising:

a body having an expandable portion at one end, which is capable of expanding upon introduction of a fluid to form a plug and which, when placed in a urethra through the natural opening thereof, and expanded, provides a urine-impermeable barrier to the flow of urine, which can only permit the passage of urine from the bladder by removal of the device;

a meatal plate attached to another end of said body, said meatal plate having a layer of adhesive thereon to anchor said meatal plate to the urethral meatus when said body is placed in the urethra, bladder neck or bladder;

means for transmitting fluid into the interior of said expandable portion of said device, from a source external to said device, to enable said expandable portion to expand upon the introduction of the fluid from the source, said expandable portion having a hollow interior, which hollow interior is in fluid communication with an opening in said body, on the end of the body opposite the end which has said expandable portion, said body defining a lumen fluidly coupling the opening and the hollow interior;

a valve in the lumen preventing flow of the fluid from the expandable portion until flow of the fluid from the expandable portion is desired by the user; and means for exerting a force on said valve to open said valve to allow deflation of the expandable portion when desired, and to enable the device to be removed in order to void.

2. The remove-to-void device according to claim 1, said adhesive comprising hydrogel adhesive.

3. The remove-to-void device according to claim 1, said body further having curved indentations on the periphery thereof.

4. A plug assembly for use in the urethra to control urinary incontinence comprising:

a housing adapted to be inserted into the natural urethral opening of a human;

a meatal plate attached to one end of said housing, said meatal plate having a layer of adhesive disposed thereon for anchoring said meatal plate to the urethral meatus when said housing is placed in the urethra, bladder neck or bladder;

means for mechanically changing the shape of said housing upon insertion of said housing into the natural opening; and means for reversing the changing of the shape of said housing, so that the wearer may remove said housing from the natural urethral opening and effect bladder evacuation.

5. The plug assembly according to claim 4, said adhesive comprising hydrogel adhesive.

6. The plug assembly according to claim 4, said housing further having curved indentations on the periphery thereof.

7. A remove-to-void device for controlling urinary incontinence comprising:

an expandable member comprising a plastic polymer possessing a first shape prior to insertion into a human body, said first shape being insufficient in size and volume to form a plug to block the flow of urine, and a second shape following insertion into a human body, said second shape being in response to the environment of the urethra, bladder neck or bladder, said second shape forming a urine-impermeable plug, said urine-impermeable plug being of sufficient size and volume so as to remain in place against the walls of the urethra, bladder neck, or bladder while blocking the flow of urine.

such that in said first shape said member is adapted to be configured in its non-expanded disposition and in said second shape said member is adapted to be configured in its expanded disposition.

said member further having a meatal plate attached at one end thereof, said meatal plate having a layer of adhesive disposed thereon so as to seal said meatal plate at the urethral meatus when said member is placed in the urethra, bladder neck or bladder.

8. The remove-to-void device according to claim 7, said adhesive comprising hydrogel adhesive.

9. The remove-to-void device according to claim 7, said member further having curved indentations on the periphery thereof.

10. A urethral plug having enhanced sealing capabilities comprising:

a body adapted to expand after insertion into a urethra of a human for internally occluding the urethra.

a meatal plate for anchoring said body to the urethral meatus, said meatal plate having a layer of adhesive disposed thereon, whereby said adhesive anchors said meatal plate at the urethral meatus such that movement of the plug is arrested.

11. The urethral plug according to according to claim 10, said adhesive comprising hydrogel adhesive.

12. The urethral plug according to claim 10, said member further having curved indentations on the periphery thereof.

13. A method of using a urethral plug having enhanced sealing capabilities comprising the steps of:

providing a urethral plug including a body having an expandable portion adapted to expand in response to a stimulus external to said plug, said body further having a meatal plate at one end thereof, said meatal plate having a layer of adhesive disposed thereon to anchor said meatal plate at the urethral meatus when said body is placed in the urethra, bladder neck or bladder;

inserting said urethral plug into the urethra of a wearer;

sealing said meatal plate against the urethral meatus via said adhesive;

introducing a stimulus to said urethral plug, causing said expandable portion to expand in response thereto, thereby blocking the flow of urine; and retaining said urethral plug in place without the movement or slippage thereof from said position until the wearer wishes to void.

14. The method according to claim 13, further comprising anchoring said urethral plug at the urethral meatus.

15. The method according to claim 13, further comprising removing said urethral plug to void the bladder.

16. The method according to claim 13, wherein said stimulus comprises the introduction of a fluid through said body to expand said expandable portion.

17. The method according to claim 13, wherein said stimulus comprises the introduction of a mechanical force on said body to expand said expandable portion.

18. A method of using a urethral plug having enhanced sealing capabilities comprising:

providing a urethral plug including a body having an expandable portion adapted to expand in response to a stimulus, said body further including a meatal plate at one end thereof, said meatal plate having a layer of adhesive disposed thereon for anchoring said meatal plate at the urethral meatus when said body is placed in the urethra, bladder neck or bladder;

inserting said urethral plug into the urethra of a wearer;

sealing said meatal plate against the urethral meatus via said adhesive;

introducing a stimulus to said urethral plug, causing said expandable portion to expand in response thereto, thereby blocking the flow of urine; and retaining said urethral plug in place without the movement or slippage thereof from said position until the wearer wishes to void.

19. The method according to claim 18, further comprising anchoring said urethral plug at the urethral meatus.

20. The method according to claim 18, further comprising removing said urethral plug to void the bladder.

21. The method according to claim 18, wherein said stimulus is the introduction of a temperature greater than the temperature of said urethral plug, causing the expansion of said expandable portion.

22. The method according to claim 18, further comprising providing adhesive on said body of said urethral plug.

23. The method according to claim 22, further comprising sealing said body against the urethra, bladder neck, or bladder wall via said adhesive.

* * * * *